United States Patent [19]

Graham

[11] Patent Number: 5,447,727
[45] Date of Patent: Sep. 5, 1995

[54] WATER-ABSORBENT POLYMER HAVING IMPROVED PROPERTIES

[75] Inventor: Andrew T. Graham, Midland, Mich.

[73] Assignee: The Dow Chemical Company, Midland, Mich.

[21] Appl. No.: 960,675

[22] Filed: Oct. 14, 1992

[51] Int. Cl.⁶ .................. C08F 220/20; A61F 13/00; A61K 9/44
[52] U.S. Cl. .................. 424/487; 424/443; 526/323; 526/326; 526/318.3; 526/330; 525/329.5
[58] Field of Search .............. 526/323, 326, 323.1, 526/322, 318.3, 323.2, 330, 306, 307.1, 330.3, 330.5, 384, 385; 424/487, 443

[56] References Cited

U.S. PATENT DOCUMENTS 4,734,478 3/1988 Tsubakimoto et al. ............ 527/300
5,026,800 6/1991 Kimura et al. ...................... 526/213

FOREIGN PATENT DOCUMENTS 0450924 9/1991 European Pat. Off. .
3000213 9/1981 Germany .................. 526/327

Primary Examiner—Peter F. Kulkosky
Attorney, Agent, or Firm—John H. Roberts

[57] ABSTRACT

The subject invention provides a surface-crosslinked water-absorbent polymer having improved properties. The subject invention further pertains to a process for preparing such a polymer. Through the use of a preferred primary crosslinking agent coupled with surface crosslinking, desirable absorptive properties are achieved. Suitable primary crosslinking agents include methylenebisacrylamide, bis(acrylamido)acetic acid and its salts, allyl acrylate, allyl methacrylate and esters or amides having both a vinyl and an allyl functionality.

25 Claims, No Drawings

WATER-ABSORBENT POLYMER HAVING IMPROVED PROPERTIES

FIELD OF INVENTION

The subject invention pertains to a surface-crosslinked water-absorbent polymer having improved properties. The subject invention further pertains to a process for preparing such a polymer. The subject invention further pertains to a method of using such a polymer.

BACKGROUND OF INVENTION

Water-swellable polymers are us,ed as constituents in personal care devices which absorb bodily fluids, such as sanitary napkins, incontinent devices and disposable baby diapers. Examples of such polymers are disclosed in U.S. Pat. Nos. 3,926,891; 4,190,562; and 4,293,609.

Various processes are known for producing absorbent polymers. For example, U.S. Pat. No. 4,833,222 teaches a process for preparing an absorbent polymer from a neutralized monomer with a surface-active agent. U.S. Pat. No. 4,808,637 teaches the uniform reaction of acrylic acid, an alkali metal salt of carbonic acid, aluminum acetate, sodium sulfate and water, preferably using microwave radiation as a heat source to initiate polymerization.

Another process comprises the steps of preparing a reaction mixture consisting essentially of particular amounts of polymerizable acid group-containing monomers, crosslinking agent and optionally free radical initiator in an aqueous medium and thereafter polymerizing and neutralizing at least a portion of the acid functional groups.

Absorbent polymers used in personal care devices are characterized by certain performance properties, including centrifuge capacity, absorbence under load, shear modulus, and percent extractables.

U.S. Pat. No. 4,666,983 discloses an absorbent article obtained by mixing 100 parts by weight of an absorbent resin powder having a carboxyl group with 0.0001 to 10 parts by weight of a crosslinking agent to crosslink the molecular chains existing at least in the vicinity of the surface of the absorbent resin powder.

U.S. Pat. No. 4,734,478 discloses a water-absorbing resin powder having the molecular chains near its surface, the resin powder being obtained by mixing 100 parts by weight of a powder of a carboxyl-containing water-absorbing resin with 0.001 to 10 parts by weight of a polyhydric alcohol and heating the mixture at a temperature of at least 100° C. to react the powder with the polyhydric alcohol, the improvement comprising conducting the mixing of the powder and the polyhydric alcohol in the presence of 0.01 to 8 parts by weight of a hydrophilic organic solvent and 0 to 8 parts by weight of water per 100 parts by weight of the powder.

U.S. patent application Ser. No. 07/866,628 discloses a process for preparing a surface crosslinked water absorbent polymer, wherein a hydrogel is contacted with a composition containing a polyhydroxy compound and a surfactant to coat the hydrogel. The coated hydrogel is then dried to form particles, is optionally ground to form sized particles, and is heated to crosslink the surface of the particles. In preferred embodiments, the hydrogels will comprise from about 15 to about 100 weight percent polymer, with the remainder comprising water. In preferred embodiment, the hydrogel is preferably in granular form, with particle sizes of about 2 cm or less being more preferred. The composition which contains the polyhydroxy compound and the surfactant will preferably contain from about 0 to about 99 percent water and from about 0 to about 50 weight percent organic solvent.

Japanese Kokai Publication 84632/1981 discloses an absorption agent consisting of a crosslinked poly(alkali metal acrylate) material obtained from 0.01 to 10 parts by weight of a water-soluble and/or water dispersible surfactant and 0.005 to 20 parts by weight of a water-soluble polyvalent alcohol per 100 parts by weight of an acrylic acid/acrylate based polymer composed of from 10–40 mole percent acrylic acid and 60–100 mole percent acrylate salt, wherein the polymer is formed by gel polymerization as a gel which is subsequently heated and dried.

European Patent Application 248,963 discloses a process of post treatment wherein the surface of water-absorbent resin particles are treated with polyquarternary amines to significantly increase the absorption rate and to increase the absorption under load (AUL) by 10 percent. In the disclosed process, the polyquarternary amines are applied as solutions in methanol.

European Patent Application 248,437 discloses a process for post surface crosslinking in which an aqueous solution of a water-soluble peroxide radical initiator is sprayed onto the surface of the water absorbent resin particles and the coated particles are heated. The reference alleges the achievement of additional surface crosslinking, leading to a product of improved water absorbency and water absorption rate. The reference discloses that the uniformity of penetration of the aqueous solution into the surface of the absorbent polymer may be improved by using a water soluble organic solvent such as methanol. The disclosed process suffers the disadvantage of using high levels of peroxide free radical initiators, which discolors partly neutralized polyacrylic acid, making the product less appealing for personal care applications. The disclosed process suffers the further disadvantage of increasing the amount of extractable polymer, e.g., low molecular weight water-soluble polymer, if the polymer is subjected to heat.

German Patent DE 3,713,601 discloses a process in which surface crosslinking is obtained by the addition of a crosslinker of glycidyl or polyglycidyl compounds. These crosslinking agents are not preferred in applications wherein the polymer is expected to contact human skin.

Industry would find great advantage in an aqueous fluid absorbent having improved absorbency under load and capacity. Industry would further find great advantage in a process for producing such an aqueous fluid absorbent

SUMMARY OF INVENTION

Accordingly, the subject invention provides a water-absorbent polymeric material comprising a crosslinked polymer of a partially neutralized $\alpha,\beta$-ethylenically unsaturated monomer, the crosslinked polymer being crosslinked with a primary crosslinking agent selected from the group consisting of methylenebisacrylamide, bis(acrylamido)acetic acid and its salts, allyl acrylate, allyl methacrylate and esters or amides having both a vinyl and an allyl functionality, the crosslinked polymer being additionally crosslinked with a surface crosslinking agent, whereupon the molecular chains existing in the vicinity of the surface of the polymer are crosslinked.

The subject invention further provides a process for preparing an aqueous fluid absorbent material comprising:

(a) preparing a crosslinked polymer of a partially neutralized $\alpha,\beta$-ethylenically unsaturated monomer, the crosslinked polymer being crosslinked with a primary crosslinking agent selected from the group consisting of methylenebisacrylamide, bis(acrylamido)acetic acid and its salts, allyl acrylate, allyl methacrylate and esters or amides having both a vinyl and an allyl functionality;

(b) contacting the crosslinked polymer with a surface crosslinking agent under conditions such that the surface crosslinking agent coats the crosslinked polymer without substantial penetration into the interior of the crosslinked polymer to form a coated crosslinked polymer; and (c) heating the coated crosslinked polymer under conditions such that the surface crosslinking agent reacts with crosslinked polymer so as to crosslink the surface of the coated crosslinked polymer.

Through the unique combination of the preferred primary crosslinking agents expressed in the claims coupled with surface crosslinking, an improved balance of absorptive properties, e.g., absorption under load (AUL) and capacity, has been realized. The resultant compositions will afford high performance in any application in which aqueous fluid absorbents are used. In particular, the compositions of the subject invention will find great utility in personal care devices, where it is critical that the polymer have the capacity to hold substantial quantities of fluid, and retain such fluids upon the exertion of pressure, e.g., upon sitting.

DETAILED DESCRIPTION

Generally, water absorbent resin particles are prepared by either a gel polymerization process or by a reverse suspension polymerization process, both of which are well-known.

In gel polymerization processes, monomers are polymerized in aqueous solution. Certain additives, such as crosslinking agents and surfactants, may be incorporated into the monomer mixture. The product of the polymerization process is a hydrogel, which is a water-swollen form of the polymer containing at least about 5 weight percent water. Generally, this hydrogel is subjected to mechanical means for reducing the particle size to granulate the hydrogel. Thereafter, the hydrogel is dried to remove the water. The particles are then typically subjected to further mechanical means of particle size reduction and classification including chopping, grinding, and sieving.

Surface crosslinked, as used herein, refers to absorbent resin polymer particles which are contacted with a crosslinking agent after completion of polymerization under conditions such that the particles are coated at or near the surface and the particles are exposed to conditions such that the surface crosslinking agent reacts with carboxyl groups at or near the surface of the particle to crosslink the water absorbent resin.

As will be set forth in greater detail below, the surface crosslinking agent may be applied at nearly any stage in the production process. For instance, the surface crosslinking agent may be applied to wet hydrogel exiting the reactor having a water content from about 65 to about 80 percent; to partially dried hydrogel having a water content between about 15 and about 35 percent; to more fully dried hydrogel having a water content between about 5 and about 15 percent; or to a polymer powder, having a water content less than about 5 percent.

The water-swellable or lightly crosslinked hydrophilic polymers that are usefully used in the present invention can be any of the known hydrophilic polymers which are capable of absorbing large quantities of fluids. In particular, water-absorbent polymers useful in this invention are water-absorbent polymers which contain carboxyl moieties. Preferably, at least about 0.01 equivalent of carboxyl groups are present per 100 grams of the water-absorbent resin.

Among preferred carboxyl-containing water absorbent polymers are hydrolyzates of starch-acrylonitrile graft copolymers, partially neutralized products of starch-acrylic acid graft copolymers, saponification products of vinyl acetate acrylic ester copolymers, hydrolyzates of acrylonitrile copolymers, crosslinked products of hydrolyzates of acrylonitrile copolymers, hydrolyzates of acrylamide copolymers, crosslinked products of hydrolyzates of acrylamide copolymers, partially neutralized products of polyacrylic acids and crosslinked products of partially neutralized polyacrylic acids.

Examples of some suitable polymers and processes for preparing them are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; and 4,190,562, the relevant portions of which are incorporated herein by reference. Such hydrophilic polymers are prepared from water-soluble $\alpha,\beta$-ethylenically unsaturated monomers such as monocarboxylic acids, polycarboxylic acids, acrylamide and their derivatives.

Suitable $\alpha,\beta$-ethylenically unsaturated monomers include, for example acrylic acid, methacrylic acid, crotonic acid, isocrotonic acid and alkali metal salts and ammonium salts thereof; maleic acid, fumaric acid, itaconic acid, acrylamide, methacrylamide and 2-acrylamido-2-methyl-1-propane sulfonic acid and its salts. The preferred monomers include acrylic acid and methacrylic acid and their respective salt forms such as alkali metal or ammonium salts.

The water-soluble monomers useful in the present invention may be used in amounts ranging from about 10 percent to about 80 percent by weight based on the total weight of the aqueous monomer solution. Preferably, the amount ranges from about 20 percent to about 60 percent based on the total weight of the aqueous monomer solution.

Optionally, the minor amounts of other water-soluble, unsaturated monomers, such as alkyl esters of the acid monomers, e.g., methyl acrylate or methyl methacrylate may be present. In addition, certain grafting polymers, such as, for example, polyvinyl alcohol, starch and water soluble or swellable cellulose ethers may be employed to prepare products having superior properties. Such grafting polymers, when employed, are used in amounts up to about 10 weight percent based on the $\alpha,\beta$-ethylenically unsaturated monomer. Further, it may be advantageous to include a chelating agent to remove trace metals from solution, e.g., when a metal reaction vessel is employed. One such chelating agent is VERSENEX V-80 (an aqueous solution of the pentasodium salt of diethylenetriamine pentacetic acid) (Trademark of The Dow Chemical Company). Such chelating agents, when employed, are generally used in amounts between about 100 and about 2000 ppm based on the α,β-ethylenically unsaturated monomer.

It is desirable to obtain a level of conversion of monomer to polymer of at least about 95 percent. The polymerization may be carried out using acid monomers that are not neutralized or that have been neutralized or partially neutralized prior to the polymerization. Neutralization is conveniently achieved by contacting the aqueous monomer with an amount of basic material sufficient to neutralize between about 20 and about 95 percent of the acid groups present in the acid monomers. Preferably, the amount of basic material will be sufficient to neutralize between about 40 percent and 85 percent, and most preferably between about 55 percent and about 75 percent of the acid groups present in the acid monomers. When pre-neutralizing the monomer solution, it is important to control the neutralization conditions so that the heat of neutralization does not cause the premature polymerization of the monomer mixture. The neutralization is advantageously carried out at temperatures below about 40° C. preferably at temperatures below about 35° C.

Compounds which are useful to neutralize the acid groups of the monomer are typically those which will sufficiently neutralize the acid groups without having a detrimental effect on the polymerization process. Such compounds include alkali metal hydroxides, alkali metal carbonates and bicarbonates. Preferably, the material used to neutralize the monomer is sodium or potassium hydroxide or sodium carbonate or potassium carbonate. In determining the desired degree of neutralization, care must be taken to ensure that the pH of the resulting crosslinked absorbent polymer, which will be contacted with or dispersed in an aqueous fluid to be absorbed, is maintained in a range appropriate for the applications for which the polymer is intended. Alternatively, the polymerization may be carried out employing unneutralized monomers and thereafter neutralizing, as is known in the art.

Conveniently, a conventional vinyl addition polymerization initiator is used in the polymerization of the water-soluble monomers and the crosslinking agent. A free radical polymerization initiator which is sufficiently soluble in the monomer solution to initiate polymerization is preferred. For example, water soluble persulfates such as potassium persulfate, ammonium persulfate, sodium persulfate, and other alkali-metal persulfates, hydrogen peroxide and water soluble azo-compounds such as 2,2'-azobis (2-amidino-propane·HCL) may be used. Some of these initiators, such as hydrogen peroxide, can be combined with reducing substances such as sulfites or amines to form known redox type initiators. The total amount of initiators used may range from about 0.01 to about 1.0 weight percent, preferably about 0.01 to about 0.5 weight percent, based on the total weight of α,β-ethylenically unsaturated monomer reactants.

The water-absorbent resin will preferably be lightly crosslinked to render it water-insoluble. The desired crosslinked structure may be obtained by the copolymerization of the selected water-soluble monomer and a crosslinking agent possessing at least two polymerizable double bonds in the molecular unit. The crosslinking agent is present in an amount effective to crosslink the water-soluble polymer. The preferred amount of crosslinking agent is determined by the desired degree of absorption capacity and the desired strength to retain the absorbed fluid, i.e., the desired absorption under load (AUL). Typically, the crosslinking agent is used in amounts ranging from about 0.0005 to about 5 parts by weight per 100 parts by weight of α,β-ethylenically unsaturated monomer used. More preferably, the amount ranges from about 0.1 to about 1 part by weight per 100 parts by weight of the α,β-ethylenically unsaturated monomer. If an amount over about 5 parts by weight of crosslinking agent per 100 parts is used, the resulting polymer has too high a crosslinking density and exhibits a reduced absorption capacity and increased strength to retain the absorbed fluid. If the crosslinking agent is used in an amount less than about 0.0005 part by weight per 100 parts, the polymer has too low a crosslinking density, and when contacted with the fluid to be absorbed becomes sticky and exhibits a lower initial absorption rate.

While the crosslinking agent will typically be soluble in the aqueous solution of the α,β-ethylenically unsaturated monomer, the crosslinking agent may be merely dispersible in such a solution, without negative implications. The use of such dispersing agents is disclosed in U.S. Pat. No. 4,833,222, the relevant portions of which are incorporated herein by reference. Suitable dispersing agents include carboxymethyl cellulose suspending aids, methyl cellulose, hydroxypropyl cellulose, and polyvinyl alcohol. Such dispersing agents are typically provided at a concentration between about 0.005 and about 0.1 weight percent, based on the total weight of α,β-ethylenically unsaturated monomer reactants.

As noted in U.S. Ser. No. 756,731, the relevant portions of which are incorporated herein by reference, a certain class of crosslinking agents yields particularly preferred absorptive properties. Such preferred crosslinking agents include methylenebisacrylamide, bis(acrylamido)acetic acid and its salts, allyl acrylate, allyl methacrylate and esters or amides having both a vinyl and an allyl functionality. It has now been discovered that when polymers prepared with the preferred crosslinking agents are further surface crosslinked with a polyhydroxy compound, absorptive properties superior to those noted in U.S. Ser. No. 756,731 are achieved.

In a preferred embodiment for making polymers useful in the practice of this invention, an aqueous solution of the α,β-ethylenically unsaturated monomer in the partially neutralized form, the crosslinking agent, the initiator and a grafting polymer substrate, if desired, is prepared.

The polymerization of the mixture may be initiated by elevating the temperature of the mixture containing the initiator or by using a redox-type initiator as described above. Generally, the temperature at which polymerization will begin ranges from about 20° C. to about 45° C. The temperature at which the polymerization is carried out is highly dependent on the type of monomers used and the specific initiator system employed. Preferably, the maximum temperature of polymerization ranges from about 50° C. to about 100° C., most preferably from about 60° C. to about 100° C. The method by which the temperature of the polymerization is controlled is not critical so long as sufficient cooling is present to remove the heat which is generated during the polymerization.

The resultant hydrogel typically contains from about 20 to about 35 weight percent water-absorbent polymer and from about 65 to about 80 percent water. The hydrogel is typically initially mechanically sized to form sized hydrogel particles having a reduced size prior to drying. Typically, such sized hydrogel particles have an average diameter less than about 2 cm.

The sized hydrogel particles are typically dried using means well-known in the art. Such drying means include fluidized bed driers, rotary driers, forced air ovens, through circulation band driers, etc. In some instances, drying will occur in two or more stages. In two-stage drying, the sized hydrogel particles are partially dried in the first stage, e.g., the size hydrogel particles are dried to less than about 10 percent moisture level, preferably about a 5 percent moisture level. During the initial drying, the hydrogel particles tend to fuse together to form a sheet. In two-stage driers, the partially dried hydrogel sheets are broken to form pieces which are very roughly about 10 cm × 10 cm × 2 cm in dimension. Such pieces are then more fully dried in the second stage, e.g., are dried to a moisture level less than about 5 percent. Following the completion of drying the pieces are more fully sized to form particles having an average diameter less than about 0.8 mm.

The polymer particles are surface crosslinked with a suitable surface crosslinking agent. Such crosslinking agents include polyhydroxyl compounds, polyglycidyl ether compounds, polyfunctional aziridine compounds, polyfunctional amine compounds and polyfunctional isocyanate compounds, with polyhydroxy compounds being especially preferred.

The polyhydroxy compound which is used as a surface crosslinking agent is a compound which contains at least two hydroxyl groups which are capable of readily reacting with the carboxyl groups of the water-absorbent resin of the hydrogel. Suitable polyhydroxy compounds will not volatilize or degrade at the temperature of heating. Preferably, the polyhydroxy compound used in this invention is selected from the group consisting of glycol, diethylene glycol, triethylene glycol, polyethylene glycols, glycerol, polyglycerol, polyethoxylated glycerol, propylene glycol, polypropylene glycols, diethanolamine, triethanolamine, polyethylene oxide, propane diol, butane diol, hydroxy terminated oxyethylene-oxypropylene block copolymers, trimethylolpropane, pentaerythritol, sorbitol, mannitol, sugars, sugar derivatives, polyoxyethylene sorbitol derivatives, polyoxyethylenelanolin derivatives, polyethoxylated sorbitol lanolin derivatives and the like. More preferred polyhydroxy compounds include diethylene glycol, triethylene glycol, glycerol, polyethoxylated glycerol, polyethylene oxide, propylene glycol, trimethylolpropane, pentaerythritol, sorbitol, and polyethylene glycol. An especially preferred polyhydroxy compounds is glycerol.

Specific examples of the polyglycidyl ether compounds are ethylene glycol diglycidyl ether and glycerin diglycidyl ether.

Specific examples of the polyfunctional aziridine compounds are 2,2-bishydroxymethylbutanol-tris[3-(1-aziridinyl)propionate], sold under the tradename Chemitite PZ-33; 1,6-hexamethylenediethyleneurea, sold under the tradename Chemitite HZ-22; and diphenylmethanebis-4,4'-N,N'-diethyloneurea, sold under the tradename Chemitite DZ-22, all of which are manufactured by Nippon Shokubai Kagaku Kogyo Co., Ltd.

Specific examples of the polyfunctional amines are ethylenediamine, triethylenetetramine, tetraethylenepentamine, pentaethylenehexamine, and polyethyleneamine.

The surface crosslinking agent is present in an amount effective to crosslink the surface of the polymer. Such amount is determined by the desired capacity and AUL of the final polymer. Ideally, such amount should significantly improve the gel strength of the polymer, as evidenced by an increased absorption under load (AUL), while not significantly reducing the capacity of the resin. Typically, the surface crosslinking agent is used in amounts ranging from about 0.00002 to about 10 parts by weight of the essentially dried absorbent resin product. More preferably, the amount ranges from about 0.0002 to about 0.005 parts by weight per 1 part by weight of dried absorbent resin product, i.e., from about 200 to about 5000 ppm based on the weight of the dried absorbent resin product. Preferably, the surface crosslinking agent will be provided in an amount of at least about 300 ppm, more preferably at least about 500 ppm, and more preferably at least about 1000 ppm, and most preferably at least about 3000 ppm based on the weight of the dried polymer.

The surface crosslinking agent may be applied at any stage of the production process. For example, the surface crosslinking agent may be applied to the wet hydrogel exiting the reactor; to the partially dried hydrogel, e.g., to the gel having passed through the first stage of a two stage dryer; to more fully dried hydrogel, e.g., to the gel having passed through the second stage of a two stage dryer; to the polymer powder having a moisture content less than about 5 weight percent; or at any point in between.

Regardless of the point at which application of the surface crosslinking agent occurs, the surface crosslinking agent may be applied either neat, or in conjunction with water and/or an organic solvent. Preferably, the compositions containing the surface crosslinking agent will contain from about 0 to about 99 percent by weight water, from 0 to 50 percent organic solvent. More preferably, the compositions will contain from about 0 to about 50 percent water, and no organic solvent. Most preferably, the compositions will contain no water and no organic solvent, i.e., the surface crosslinking agent will be applied neat.

Further, the composition containing the surface crosslinking agent may include a surfactant to facilitate a homogeneous distribution of the surface crosslinking agent on the polymer particles, to improve the processability of the coated polymer particles, to reduce the tendency of the dried powder to agglomerate when exposed to humid air or water, and/or to bind fine dust of the water-absorbent resin.

The use of such surfactants is addressed in U.S. Ser. No. 866,628, the relevant portions of which are incorporated herein by reference. Suitable surfactants are nonionic surfactants which are dispersible in water and which have an HLB value in the range of from about 3 to about 10. Preferred surfactants are those selected from the group of sorbitan fatty acid esters, polyoxyethylene sorbitan fatty acid esters, glycerol or polycglycerol fatty acid esters, polyoxyethylene alkyl ethers, polyoxyethylene alkylphenol ethers, polyoxyethylene acyl esters, and sucrose fatty acid esters or modified surface active polyesters.

Such surfactants are preferably used in an amount from about 0.01 to about 2 parts per 100 parts by weight of the water-absorbent resin, more preferably from about 0.075 to about 0.5 parts per 100 parts by weight of the water-absorbent resin.

When the surfactant has two or more hydroxyl moieties capable of reacting with carboxyl moieties, the surfactant can be used both as a polyhydroxy compound, e.g., surface crosslinking agent, and as a surfactant. In other words, certain polyhydroxy compounds which serve as surface crosslinking agents may also serve as surfactants. One example of such a polyhydroxy compound is a polyethoxylated sorbitol lanolin derivative.

The hydrogels/powders and the surface crosslinking agent should be contacted under conditions such that the particles can be coated with the surface crosslinking agent, but such that the surface crosslinking agent does not significantly diffuse into the internal structure of the water-absorbent resin particle. Preferably, such contacting will be conducted with some form of mechanical distribution, such that adequate distribution of the surface crosslinking agent on the water-absorbent resin particles occurs. Grinding, followed by moderate stirring, shaking, or even a short distance of conveying in a screw-conveyer is sufficient for such adequate distribution of the surface crosslinking agent over the hydrogel particles, particularly if the hydrogel particles are at an elevated temperature. For instance, neat surface crosslinking agent may be applied to the partially dried sized hydrogel particles exiting the first stage of a two-stage drier, whereupon the surface crosslinking agent is distributed over the surfaces of the particles during a mechanical sizing operation that occurs after the completion of drying but prior to heat treatment.

The temperature of contacting can be any temperature at which the surface crosslinking agent does not significantly react with the carboxyl moieties of the absorbent resin polymer. Such temperatures are typically at least from about 20° to about 150° C. It should be noted that elevated temperatures, i.e., those above ambient temperatures, improve the speed of coating of the hydrogel particles.

Upon application of the surface crosslinking agent to a hydrogel, the hydrogel is dried to a moisture level less than about 5 weight percent. Preferably, the hydrogel is dried to a moisture level from about 1 to about 5 weight percent. Should the surface crosslinking agent be applied to the hydrogel prior to any drying, e.g., straight from the reactor, the drying will obviously require more time than should the surface crosslinking agent have been applied at some point downstream from the reactor, e.g., after passage through the first stage of a two-stage drier.

The temperature at which the drying takes place is a temperature high enough such that the water and any optional organic solvent is removed in a reasonable time period, yet not so high as to react the surface crosslinking agent with the carboxyl moieties of the water-absorbent resin. Preferably, the temperature of the water-absorbent resin particles during drying is about 170° C. or less. More preferably, the temperature during drying is from about 100° to about 170° C., most preferably from about 150° to about 170° C.

The drying time should be sufficient to remove substantially all of the water and the optional solvent in a reasonable time period, and will depend on the drying system employed. Typically, the drying will reduce the moisture level of the hydrogel to a level from about 1 to about 5 weight percent.

The coated hydrogel will preferably be subjected to mechanical particle reduction means, e.g., chopping, cutting, and/or grinding. Such mechanical particle reduction means serve to reduce the particle size of the water-absorbent resin particles to a particle size acceptable in the ultimate end use. Such mechanical particle reduction will further preferably serve to distribute the surface crosslinking agent over the mechanically reduced particles. It is for this reason that coating should preceed and heat treatment should follow final sizing.

In a preferred mode, the coated absorbent resin particles are sized by first chopping, and then grinding. In a preferred embodiment, the resultant particle size is less than about 2 mm, and is more preferably less than about 0.8 mm. Preferably, the resultant particles have a size of at least about 0.04 mm, more preferably at least about 0.07 mm, and most preferably greater than about 0.1 mm.

In the case wherein the surface crosslinking agent is applied to a powder, e.g., to a sized product having a moisture content less than about 5 weight percent, the surface crosslinking agent is applied with mixing by a ribbon mixer, screw mixer, fluidized bed mixer, V-shaped rotating mixer, etc. The mixed dried powder is then heat treated in the above manner. Application of the surface crosslinking agent, mixing, and heat treatment may advantageously occur simultaneously, e.g., in the case of a fluidized bed mixer.

After drying and particle size reduction, the water-absorbent resin particles are subjected to conditions such that the polyhydroxy compound reacts with the carboxyl moieties of the water absorbent resin, so as to crosslink the water-absorbent resin at or near the surface of the particles. In particular, the dried and coated water-absorbent resin particles are heated for a time sufficient to increase the modulus and/or the absorbency under load. Such heat treatment is preferably carried out at a temperature of at least about 170, more preferably of at least 180, and most preferably of at least about 190° C. Such heat treatment is preferably carried out at a temperature of less than about 250°, more preferably less than about 230°, and most preferably less than about 210° C.

The time period for heat treatment should be sufficient for the surface crosslinking agent present at or near the surface of the absorbent resin to react with the carboxyl moieties. The exact times of heat treatment required will be affected by the equipment chosen, and can be determined empirically by examination of product properties. Preferably, the time is at least about 3 minutes, and more preferably at least about 5 minutes. If the time is too long, the process becomes uneconomical and a risk is run that the absorbent resin may be damaged. Preferably, the maximum time of heating is about 150 minutes or less, more preferably 60 minutes or less.

The method of heat treatment is not critical. For example, forced air ovens, fluidized bed heaters, heated screw conveyors, and the like may be successfully employed. If desired, the coated and heated polymer may be remoisturized for ease in handling.

While the subject invention has been described largely with respect to polymers prepared by gel polymerization processes, it should be recognized that the invention also applies to polymers prepared by suspension polymerization processes. For instance, an absorbent resin may be obtained by dispersing an aqueous solution of acrylic acid/acrylate containing a water-soluble free radical polymerization initiator and one of the primary crosslinking agents set forth above in an alicyclic and/or an aliphatic hydrocarbon solvent in the presence of a suspending aid, and subjecting the mixture to suspension polymerization. The resultant polymer beads are dried to remove residual solvent. The surface crosslinking agent is then applied to the dried beads with mixing, such as a ribbon mixer, a screw mixer, a rotating disc mixer, a fluidized bed mixer, a V-shaped rotating mixer, etc. The mixed dried beads are then heat treated in the manner specified above. Application of the surface crosslinking agent, mixing, and heat treatment may advantageously occur simultaneously, e.g., in the case of a fluidized bed mixer.

The following examples are provided for the purpose of explanation rather than limitation. Unless otherwise indicated, sixty minute 0.3 psi AUL was measured as described in European Patent Application EP 339,461-Al; sixty minute 0.6 psi AUL was measured in the manner described for the measurement of 0.3 psi AUL, except that a 0.6 psi pressure rather than a 0.3 psi pressure was applied and except that the test time was 90 minutes rather than 60 minutes; centrifuge capacity was determined as described in U.S. Pat. No. 4,286,082 except that an absorption time of 30 minutes rather than 3 to 5 minutes was employed; fish eyes formation was determined as described in U.S. Pat. No. 4,666,983; and the extractables and modulus were determined as described in U.S. Reissue patent 32,649, with the relevant portions of each of the cited references being incorporated herein by reference. Further, vortex time was taken as the time for the vortex to disappear when 2 grams of polymer was added to 50 grams of a 0.9 percent saline solution contained in a 100 mL beaker while the saline solution was being stirred with about a ½ to 1 inch vortex on a magnetic mixer. Gel blocking was noted in the vortex rate test if the powdered absorbent resin did not fully disperse into the saline solution. Percent moisture was determined by drying a portion of polymer at 135° C. for about 60 hours, and using the weights before and after drying to calculate the percent moisture of the sample.

EXAMPLE ONE

To a beaker, 300 grams of acrylic acid, 0.75 grams VERSENEX V-80 chelating agent (available from the Dow Chemical Company), 144 grams sodium carbonate, and enough water to bring the final reactor solids to 32 percent were added. To this, 145 grams of a 10 percent aqueous solution of polyvinyl alcohol was added and was thoroughly mixed. Then, 0.63 gram allyl methacrylate was added. The resultant mixture was transferred to a reactor, which was purged with nitrogen to remove air. To the reactor, 4.8 mL of a 10 percent aqueous solution of sodium persulfate and 0.63 mL of a 30 percent aqueous solution of hydrogen peroxide were added. The contents of the reactor were mixed for one to two minutes. Then, 0.6 mL of a 10 percent aqueous solution of sodium erythorbate was added. Polymerization proceeded to completion in about four hours.

The gel was dried in a standard commercial forced air oven. The majority of the particles of the dried resin mass were greater than 0.5 cm in length and breadth. When dry, a portion of the resin mass was ground and screened to pass through a 100 mesh sieve, and was saved as Comparative Example 1-A. A portion of the material of Comparative Example 1-A was heat treated for 35 minutes at 210° C. to form Comparative Example 1-B. The remainder of the unground and unscreened material was treated by weighing portions of the dried resin mass and weighing enough glycerine onto each portion to give the indicated amount of glycerin based on dry solids. Samples of each portion were ground and screened to pass through a 100 mesh sieve, and were heat treated for 35 minutes at 210° C. to form Examples 1A and 1B.

The results of Examples 1A, 1B, and Comparative Examples 1-A and 1-B are set forth in Table One.

EXAMPLE TWO

To a beaker, 300 grams of acrylic acid, 0.75 grams VERSENEX V-80 chelating agent (available from the Dow Chemical Company), 144 grams sodium carbonate, and enough water to bring the final reactor solids to 32 percent were added. To this, 145 grams of a 10 percent aqueous solution of polyvinyl alcohol was added and was thoroughly mixed. Then, 0.63 gram trimethylolpropanetriacrylate was added. The resultant mixture was transferred to a reactor, which was purged with nitrogen to remove air. To the reactor, 4.8 mL of a 10 percent aqueous solution of sodium persulfate and 0.63 mL of a 30 percent aqueous solution of hydrogen peroxide were added. The contents of the reactor were mixed for one to two minutes. Then, 0.6 mL of a 10 percent aqueous solution of sodium erythorbate was added. Polymerization proceeded to completion in about four hours.

The gel was dried in a standard commercial forced air oven. The majority of the particles of the dried resin mass were greater than 0.5 cm in length and breadth. When dry, a portion of the resin mass was screened to be pass through a 100 mesh sieve and was saved as Comparative Example 2-A. A portion of the material of Comparative Example 2-A was heat treated for 35 minutes at 210° C. to form Comparative Example 2-B. The remainder of the unground and unscreened material was treated by weighing portions of the dried resin mass and weighing enough glycerine onto each portion to give the indicated amount of glycerin based on dry solids. Samples of each portion were ground and screened to pass through a 100 mesh sieve, and were heat treated for 35 minutes at 210° C. to form Examples 2A and 2B.

The results of Examples 2A, 2B, and Comparative Examples 2-A and 2-B set forth in Table One.

TABLE ONE

| Sample | Fish Eyes | Vortex Time (sec) | Gel Block | 30 sec capacity (g/g) | 60 sec. capacity (g/g) | 10 min. capacity (g/g) |
| --- | --- | --- | --- | --- | --- | --- |
| Comparative 1-A | Yes | >200 | Yes | 6.3 | 9.9 | 21.4 |
| Comparative 1-B | No | 30 | Yes | | | |
| 1A | No | 29 | Yes | 30.1 | 35.1 | 42.2 |
| 1B | No | 10 | No | 29.7 | 37.3 | 44.7 |
| Comparative 2-A | Yes | >200 | Yes | 6.9 | 8.1 | 29.6 |
| Comparative 2-B | No | 140 | Yes | | | |
| 2A | No | 17 | No | 28.4 | 35.0 | 42.9 |
| 2B | No | 11 | No | 29.9 | 37.3 | 42.8 |

Examples One and Two demonstrate that improved absorption rate and reduced fish eye formation and gel blocking can be obtained with a surface crosslinking agent is applied to the dry or partially dry absorbent resin polymer mass prior to grinding. The surface crosslinking agent can be applied in a range of at least from about 300 to about 3000 ppm, based on dry solids.

EXAMPLE THREE

To a reactor, 48 pounds acrylic acid, 53.4 grams allyl methacrylate, 26.5 pounds of an 8 percent aqueous solution of VINOL 523 poly(vinyl alcohol) solution (available from Air Products Corp.), 22 pounds sodium carbonate, 98 pounds water, and 29 grams VERSENEX V-80 chelating agent were added and mixed. To the mixture, 37 grams sodium persulfate in an aqueous solution and 50.8 grams of a 30 percent aqueous solution of hydrogen peroxide were added and mixed. Next, 3.3 grams of sodium erythorbate in an aqueous solution were added. The reactor was then sparged with nitrogen. The polymerization began and was essentially complete in about 2 hours.

The resultant gel was separated into five parts for drying and coating with glycerin. Glycerin was added dropwise to the gel, at the drying stage extrapolated from the indicated percent moisture of the sample, in order to give about 500 ppm glycerine, based on the final dried weight of the polymer. When the glycerin was added to the polymer resin mass, samples of the resin mass were taken. Following addition of the glycerin, the samples were dried to a moisture level of 5 percent and were ground and screened. A screen cut between 20 and 140 mesh was taken for use in capacity, AUL, and extractables determinations. A fines cut less than 140 mesh was taken for use in fish eye and vortex time determinations. The samples were heat treated in a commercial forced air oven for 40 minutes at 200° C., resulting in Examples 3A, 3B, 3C, 3D, and 3E. Comparative Example 3-A represents an uncoated, non-heat treated sample of Example 3A. Comparative Example 3-B represents the uncoated sample of Comparative Example 3-A which has been heat treated.

The results of Examples 3A, 3B, 3C, 3D, 3E, and Comparative Examples 3-A and 3-B are set forth in Table Two.

EXAMPLE FOUR

To a reactor, 49 pounds acrylic acid, 37.7 grams trimethylolpropanetriacrylate, a solution of 22.5 pounds sodium carbonate in water, sufficient additional water such that the total amount of water equaled 115 pounds were added and mixed. To the mixture, 15 grams VERSENEX V-80 chelating agent and 103 grams of a 5 percent aqueous solution of polyvinyl alcohol were added and mixed. To the mixture, 38.5 grams of sodium persulfate in an aqueous solution and 40 grams of a 30 percent aqueous solution of hydrogen peroxide were added and mixed. Next, 3.4 grams sodium erythorbate in an aqueous solution were added. The reactor was then sparged with nitrogen. The polymerization began and was essentially complete in about 2 hours.

The resultant gel was separated into five parts for drying and coating with glycerin. Glycerin was added dropwise to the gel, at the drying stage extrapolated from the indicated percent moisture of the sample, in order to give about 500 ppm glycerine, based on the final dried weight of the polymer. At the time the glycerin was added to the polymer resin mass, samples of the resin mass were taken. Following addition of the glycerin, the samples were dried to a moisture level of 5 percent and were ground and screened. A screen cut between 20 and 140 mesh was taken for use in capacity, AUL and extractables determinations. A fines cut less than 140 mesh was taken for use in fish eye and vortex time determinations. The samples were heat treated in a commercial forced air oven for 40 minutes at 200° C., resulting in Examples 4A, 4B, 4C, 4D, and 4E. Comparative Example 4-A represents an uncoated, non-heat treated sample of Example 4A. Comparative Example 4-B represents the uncoated sample of Comparative Example 4-A which has been heat treated.

The results of Examples 4A, 4B, 4C, 4D, 4E, and Comparative Examples 4-A and 4-B are set forth in Table Two.

TABLE TWO

| Sample | Percent Moisture | Fish Eyes | Vortex Time (sec) | Capacity | 0.3 psi AUL | 0.6 psi AUL | Percent Extractables |
|---|---|---|---|---|---|---|---|
| Comparative 3-A | 5 | Yes | >150 | 34.0 | 15.5 | 9.6 | |
| Comparative 3-B | 5 | | | 35.3 | 29.2 | 14.3 | 7.66 |
| 3A | 5 | No | 13 | 34.4 | 29.9 | 18.0 | 7.96 |
| 3B | 11.4 | No | 17 | 35.0 | 29.2 | 16.5 | 7.62 |
| 3C | 59.5 | No | 17.5 | 34.6 | 29.8 | 18.1 | 7.64 |
| 3D | 63 | No | 20 | 33.5 | 29.5 | 17.6 | 7.59 |
| 3E | 202.5 | No | 17.5 | 34.1 | 30.0 | 18.3 | 7.64 |
| Comparative 4-A | 6.92 | Yes | >150 | 44.3 | 7.9 | 8.4 | 17.59 |
| Comparative 4-B | 6.92 | | | 32.9 | 23.0 | 11.6 | 12.10 |
| 4A | 6.92 | No | 15 | 30.9 | 25.1 | 16.9 | 12.39 |
| 4B | 13.38 | No | 25 | 32.2 | 22.9 | 12.0 | 12.84 |
| 4C | 37.4 | No | 24 | 31.3 | 24.0 | 13.4 | 12.08 |
| 4D | 80.4 | No | 29 | 31.8 | 24.2 | 12.9 | 11.38 |
| 4E | 208 | No | 27 | 33.4 | 22.5 | 10.9 | 11.91 |

Examples Three and Four demonstrate that the use of a preferred primary crosslinking agent improves the balance of absorptive properties and extractables, e.g., the ratio of 0.6 psi AUL to capacity increases while low levels of extractable polymer are maintained. Examples Three and Four further illustrate that the surface crosslinking agent may be applied to a polymer of different moisture levels without sacrificing this balance of properties.

EXAMPLE FIVE

In a beaker, 300 grams acrylic acid 0.75 grams VERSENEX V-80 chelating agent, 144 grams sodium carbonate, and enough water to bring the final reactor solids to 32 percent were added and mixed. To the mixture, 145 grams of a 10 percent solution of poly(vinyl alcohol) was added and thoroughly mixed. Then, 0.9 grams allyl methacrylate was added, the mixture was added to a reactor, and the reactor was purged with nitrogen. To the reactor, 4.8 mL of a 10 percent aqueous solution of sodium persulfate and 0.63 mL of a 30 percent aqueous solution of hydrogen peroxide were added and mixed for one to two minutes. Then, 0.6 mL of a 10 percent solution of sodium erythorbate were added. The polymerization began and was completed in about 4 hours.

The resultant gel was separated into four parts and was dried in a standard commercial forced air oven. When dry, one portion of the material was ground and saved as Comparative Example 5-1. Other portions of the material were treated by weighing the portions and weighing the indicated amount of glycerin onto the portions. The coated portions were placed in a food blender and were ground and screened to a 20 to 100 mesh cut. The sized and coated portions were placed in a jar and tumbled in a roller mixer for an additional 15 to 30 minutes. The samples were then placed in a forced air oven at 200° C. for 40 minutes to react the glycerin with the carboxyl groups on the absorbent resin. One of the sized portions was not coated with glycerin, but was heat treated as described, resulting in Comparative Example 5-2. The final products (Examples 5A, 5B, and 5C) and the products of the comparative examples were analyzed.

The results of Examples 5A, 5B, 5C, and Comparative Examples 5-1 and 5-2 are set forth in Table Three.

EXAMPLE SIX

Polymerizations were carried out in the same manner as described in Example 5, excepting that the glycerin was replaced with the indicated coating material. Table Four lists the coating material, the account of coating material used, and the product properties after heat treatment. Examples 6A, 6B, 6C, 6D and 6E are examples of the invention. Comparative examples 6-A1, 6-A2, 6-A3, 6-A4, and 6-A5 correspond to examples 6A, 6B, 6C, 6D and 6E, excepting that the comparative examples represent uncoated samples which have not been heat treated. Comparative examples Comparative examples 6-B1, 6-B2, 6-B3, 6-B4, and 6-B5 correspond to examples 6A, 6B, 6C, 6D and 6E, excepting that the comparative examples represent uncoated samples which have been heat treated in the manner for heat treating the samples of Examples 6A, 6B, 6C, 6D and 6E. The final products (Examples 6A, 6B, 6C, 6D and 6E) and the products of the comparative examples were analyzed.

The results of Examples 6A, 6B, 6C, 6D, 6E, of Comparative Examples 6-A1, 6-A2, 6-A3, 6-A4, 6-A5, and of Comparative Examples 6-B1, 6-B2, 6-B3, 6-B4, and 6-B5 are set forth in Table Four.

TABLE FOUR

| Coating Sample | Chemical | Coating (ppm) | 0.3 psi AUL (g/g) | 0.3 psi AUL (g/g) | Swelling Capacity (g/g) | Modulus (dynes/cm$^2$) | 0.6 psi AUL Capacity |
|---|---|---|---|---|---|---|---|
| Comparative 6-A1 | polyethylene | 0.0 | 13.6 | 9.0 | 33.1 | 22100 | 0.27 |
| Comparative 6-A2 | oxide | 0.0 | 29.5 | 19.0 | 32.9 | 38300 | 0.57 |
| 6A | (avg. mol. wt = 200) | 997 | 29.7 | 23.5 | 32.2 | 38700 | 0.72 |
| Comparative 6-B1 | polyethoxyalated | 0.0 | 9.9 | 8.5 | 35.4 | 22000 | 0.24 |
| Comparative 6-B2 | glycerol | 0.0 | 26.2 | 12.2 | 34.8 | 31500 | 0.35 |
| 6B | (avg. mol. wt = 212) | 995 | 27.5 | 18.5 | 33.3 | 34200 | 0.55 |
| Comparative 6-C1 | propylene glycol | 0.0 | 12.0 | 8.9 | 35.3 | 20200 | 0.25 |
| Comparative 6-C2 | | 0.0 | 23.8 | 12.1 | 34.5 | 28200 | 0.35 |
| 6C | | 1035 | 29.4 | 17.4 | 33.1 | 33800 | 0.52 |
| Comparative 6-D1 | polyethylene | 0.0 | 10.5 | 8.7 | 34.9 | 21300 | 0.25 |
| Comparative 6-D2 | glycol | 0.0 | 26.6 | 13.5 | 33.9 | 34500 | 0.40 |
| 6D | (avg. mol. wt. = 600) | 1991 | 26.7 | 16.4 | 33.8 | 34600 | 0.49 |
| Comparative 6-E1 | Sorbitol | 0.0 | 16.9 | 9.1 | 32.9 | | 0.28 |
| Comparative 6-E2 | (50% aqueous | 0.0 | 29.6 | 14.6 | 33.6 | | 0.43 |
| 6E | solution) | 501 | 29.8 | 18.5 | 33.5 | | 0.55 |

The data set forth in Table Four illustrates that any polyfunctional alcohol containing material would be

TABLE THREE

| Polymer Sample | Glycerine (ppm) | 0.3 psi AUL (g/g) | 0.6 psi AUL (g/g) | Swelling Capacity (g/g) | AUL (0.6) Swelling Cap |
|---|---|---|---|---|---|
| Comparative 5-1 | 0.0 | 10.0 | 9.1 | 36.4 | 0.25 |
| Comparative 5-2 | 0.0 | 25.3 | 12.4 | 35.5 | 0.349 |
| 5A | 286 | 26.2 | 16.3 | 34.0 | 0.479 |
| 5B | 648 | 28.0 | 19.8 | 33.4 | 0.593 |
| 5C | 1031 | 28.6 | 19.7 | 32.8 | 0.600 |

The difference between Comparative Examples 5-1 and 5-2 is typical of the way in which absorbent polymers made under these conditions react to heating. See U.S. Ser. No. 756,731. The effects of the surface treatment are found by comparing the results of Examples 5A through 5C. Some reduction in centrifuged capacity was observed. However, a slight increase in 0.3 psi AUL and a substantial increase in 0.6 psi AUL likewise resulted. The improvement as a result of the present invention can be seen in the improvement in AUL/-Swelling capacity in the rightmost column of Table Three.

expected to perform satisfactorily in the process of the present invention.

EXAMPLES SEVEN AND EIGHT

In a beaker, 300 grams acrylic acid 0.75 grams VERSENEX V-80 chelating agent, 144 grams sodium carbonate, and enough water to bring the final reactor solids to 32 percent were added and mixed. To the reactor, the desired crosslinking agent was added. In the case of Example Seven, 0.95 grams methylenebisacrylamide crosslinking agent was added, the mixture was added to a reactor, and the reactor was purged with nitrogen. In the case of Example Eight, 0.95 grams allyl methacrylate crosslinking agent was added, the mixture was added to a reactor, and the reactor was purged with nitrogen.

To the reactor, 4.8 mL of a 10 percent solution of sodium persulfate and 0.63 grams of a 30 percent solution of hydrogen peroxide were added and mixed for one to two minutes. Then, 0.6 grams of a 10 percent solution of sodium erythorbate were added. The polymerization began and was completed in about 4 hours.

The resultant gels were each separated into two parts and were dried in a standard commercial forced air oven. When dry, one portion of each material was ground and saved as Comparative Examples 7-1, 7-2, 8-1 and 8-2. Other portions of the material were treated by weighing the portions and weighing the indicated amount of the surface crosslinking agent onto the portions. The coated portions were placed in a food blender and were ground and screened to a 20 to 100 mesh cut. The sized products were coated with the indicated amount of coating material and were placed in a jar and tumbled in a roller mixer for an additional 15 to 30 minutes. The samples were then placed in a forced air oven at 200° C. for 40 minutes to react the hydroxyl groups of the coating materials with the carboxyl groups on the absorbent resin. The final products (Examples 7A, 7B, 7C, 7D, 8A, 8B, 8C, and 8D) and the products of the comparative examples (7-1, 7-2, 8-1, and 8-2) were analyzed.

The results of Examples 7A, 7B, 7C, 7D, 8A, 8B, 8C, and 8D and comparative examples 7-1, 7-2, 8-1, and 8-2 are set forth in Table Five.

EXAMPLE NINE

Polymerizations were conducted in the same manner as described with respect to Example 5, except that the coating material was a mixture of glycerine and water as shown in Table Six to make absorbent resins 9A, 9B, and 9C. Comparative Example 9-1 is a heat treated uncoated sample.

The results of Examples 9A, 9B, 9C and comparative example 9-1 are set forth in Table Six.

TABLE SIX

| Sample | Coating Composition | Coating ppm | AUL g/g 0.3 psi | AUL g/g 0.6 psi | Swelling Capacity g/g |
|---|---|---|---|---|---|
| Comparative 9-1 |  | 0.0 | 23.9 | 12.2 | 36.8 |
| 9A | 80% Glycerine | 514 | 26.6 | 16.9 | 34.2 |
| 9B | 65% Glycerine | 501 | 27.2 | 19.2 | 34.0 |
| 9C | 50% Glycerine | 500 | 27.2 | 16.7 | 34.8 |

The data set forth in Table Six illustrates that while the presence of water as a solvent for the coating material is not necessarily beneficial, at the levels indicated here, it does not harm the spread of the coating chemical over the surface of the absorbent resin. Despite the presence of water, the improved combination of swelling capacity and AUL of the present invention is observed.

EXAMPLE TEN

In a beaker, 310 grams of acrylic acid, 0.75 grams VERSENEX V-80 chelating agent, 144 grams sodium carbonate, and enough water to bring the final reactor solids to 32 percent were added and mixed. Then 0.10 grams allyl methacrylate was added, the mixture was added to a reactor, and the reactor was purged with nitrogen. To the reactor, 4.8 mL of a 10 percent solution of sodium persulfate and 0.63 mL of a 30 percent solution of hydrogen peroxide were added and mixed for one to two minutes. Then, 0.6 mL grams of a 10 percent solution of sodium erythorbate were added. The polymerization began and was completed in about 4 hours.

TABLE FIVE

| Sample | Coating Chemical | Coating ppm | AUL g/g 0.3 psi | AUL g/g 0.6 psi | Swelling Capacity g/g |
|---|---|---|---|---|---|
| Comparative 7-1 |  | 0 | 27.9 | 16.5 | 27.4 |
| 7A | Glycerine | 533 | 30.0 | 26.7 | 29.6 |
| Comparative 7-2 |  | 0 | 27.9 | 17.7 | 26.7 |
| 7B | polyethylene oxide (avg. mol. wt. = 200) | 587 | 31.0 | 25.3 | 30.0 |
| 7C | Diethylene glycol | 519 | 30.9 | 25.6 | 30.2 |
| 7D | polyethoxylated glycerol (avg. mol. wt. = 212) | 542 | 31.2 | 25.9 | 30.1 |
| Comparative 8-1 |  | 0 | 27.0 | 14.4 | 27.5 |
| 8A | Glycerine | 505 | 30.3 | 26.3 | 29.1 |
| Comparative 8-2 |  | 0 | 26.8 | 18.9 | 26.3 |
| 8B | polyethylene oxide (avg. mol. wt. = 200) | 536 | 29.9 | 24.0 | 28.9 |
| 8C | Diethylene glycol | 520 | 29.5 | 23.8 | 28.9 |
| 8D | polyethoxylated glycerol (avg. mol. wt. = 212) | 522 | 29.5 | 24.2 | 28.8 |

The data set forth in Table Five illustrates that polymers of the subject invention which are free of poly(vinyl alcohol) which utilize allyl methacrylate and/or methylenebisacrylamide type crosslinking agents, result in polymers having very desirable absorptive properties.

The resultant gels were dried in a standard commercial forced air oven. When dry, one portion of each material was ground and saved as Comparative Examples 10-A1, 10-B1, and 10-C1. The dried products were treated by weighing the dried resin masses, and weighing enough glycerine onto the dried resin masses to give about 500 ppm glycerin based on dry solids. The products were ground to 20 to 100 mesh, were placed in jars, and were tumbled in a roller mixer for an additional 15 to 30 minutes. Portions of the materials were heat treated in a forced air oven for times and at the temperatures indicated in Table Seven. The final products and the products of the comparative examples were analyzed.

The results of Examples 10A1, 10A2, 10A3, 10A4, 10A5, 10A6, Examples 10B1, 10B2, 10B3, 10B4, 10B5, 10B6, Examples 10C1, 10C2, 10C3, 10C4, 10C5, 10C6, and Comparative Examples 10-A1, 10-B1, and 10-C1 are set forth in Table Seven.

TABLE SEVEN

| Sample | Heating Temp. | Heating Time | AUL g/g 0.3 psi | AUL g/g 0.6 psi | Swelling Capacity g/g |
|---|---|---|---|---|---|
| Comparative 10-A1 | 200 | 35 min | 14.4 | 9.4 | 37.8 |
| 10A1 | 180 | 0 | 13.0 | 8.9 | 33.5 |
| 10A2 | | 15 min | 17.7 | 10.0 | 34.3 |
| 10A3 | | 30 min | 24.9 | 12.1 | 34.1 |
| 10A4 | | 45 min | 27.5 | 13.0 | 34.0 |
| 10A5 | | 60 min | 27.3 | 13.4 | 34.2 |
| 10A6 | | 75 min | 27.6 | 15.0 | 33.7 |
| Comparative 10-B1 | 200 | 35 min | 9.4 | 8.5 | 42.5 |
| 10B1 | 190 | 0 | 9.2 | 8.5 | 36.8 |
| 10B2 | | 15 min | 17.9 | 9.5 | 37.6 |
| 10B3 | | 30 min | 21.3 | 10.0 | 38.4 |
| 10B4 | | 45 min | 21.2 | 9.6 | 38.4 |
| 10B5 | | 60 min | 21.5 | 9.6 | 38.6 |
| 10B6 | | 75 min | 22.1 | 11.2 | 38.5 |
| Comparative 10-C1 | 200 | 35 min | 10.1 | 9.1 | 39.4 |
| 10C1 | 200 | 0 | 9.7 | 8.3 | 35.8 |
| 10C2 | | 10 min | 22.7 | 10.8 | 36.3 |
| 10C3 | | 20 min | 23.6 | 11.0 | 37.0 |
| 10C4 | | 30 min | 23.4 | 10.9 | 37.0 |
| 10C5 | | 40 min | 24.2 | 10.6 | 37.2 |
| 10C6 | | 50 min | 26.0 | 13.0 | 36.8 |

Example Ten demonstrates the applicability of heat treating temperatures between 180° and 200° C. in the practice of the subject invention. Example Ten further demonstrates the shift in product properties that occurs as a function of the time for heat treatment.

EXAMPLE ELEVEN 1900 kg of acrylic acid, 4.56 kg of trimethylolpropanetriacrylate, 475 grams of polyvinyl alcohol, 950 grams of VERSENEX V-80 chelating agent, and 1435 kg of a 50 percent aqueous solution of sodium hydroxide were combined in a vessel with enough additional water to bring the final polymer solids concentration to 35 percent. Sodium persulfate and hydrogen peroxide were added and the mixture was purged with nitrogen to remove air. A solution of ascorbic acid was added and the polymerization proceeded to completion in about 2 hours. The resultant gel was dried in a standard commercial forced air oven and was ground. A portion of the polymer was weighed into a container, and to it was added 250 grams of an 80/20 propanol/water solution containing glycerine, such that the weight of glycerine to the weight of polymer was 0.2 percent. This material was dried overnight at 100° C. Subsequently, this material was dried in an open glass container in a 180° C. oven for 40 minutes. The 0.3 psi AUL was 31.7 g/g, the centrifuge capacity was 36.1 g/g, and the 16 hour extractables were 14 percent.

EXAMPLE TWELVE

A polymerization is conducted in the same manner as described in Example Five. The gel is dried and ground using a food blender and screened to a 20 to 100 mesh cut. Glycerin is added to the powder at a 500 ppm level. The sample is tumbled for 15 to 20 minutes on a roller mixer. The samples are then placed in a forced air oven at 200° C. for 40 minutes. The 0.3 psi AUL is about 30 g/g, the centrigue capacity is about 35 g/g and the 16 hour extractables are about 8 percent. This demonstrates that the surface crosslinking agent may be applied to the sized polymer powder without sacrificing the balance of absorptive properties afforded by the subject invention.

What is claimed is:

1. A water-absorbent polymeric material comprising a crosslinked polymer of a partially neutralized $\alpha,\beta$-ethylenically unsaturated monomer, the crosslinked polymer being crosslinked with a primary crosslinking agent selected from the groups consisting of, bis(a-crylamido)acetic acid and its salts, allyl acrylate, allyl methacrylate and esters or amides having both a vinyl and an allyl functionality, the crosslinked polymer being additionally crosslinked with a surface crosslinking agent selected from the group consisting of polyhydroxy compounds, polyglycidyl ether compounds, polyfunctional aziridine compounds, polyfunctional amine compounds, and polyfunctional isocyanate compounds, whereupon the molecular chains existing in the vicinity of the surface of the polymer are crosslinked.

2. The water-absorbent polymeric material of claim 1, wherein the surface crosslinking agent is a polyhydroxy compound.

3. The water-absorbent polymeric material of claim 2, wherein the polyhydroxy compound is selected from the group consisting of diethylene glycol, triethylene glycol, glycerol, propylene glycol, trimethylolpropane, pentaerythritol, sorbitol, and polyethylene glycol.

4. The water-absorbent polymeric material of claim 2, wherein the polyhydroxy compound is glycerol.

5. The water-absorbent polymeric material of claim 1, wherein the primary crosslinking agent is allyl methacrylate.

6. The water-absorbent polymeric material of claim 1, wherein the surface crosslinking agent is provided in an amount from about 0.00025 to about 2 weight percent, based on the weight of the crosslinked polymer.

7. A process for preparing an aqueous fluid absorbent material comprising:

(a) preparing a crosslinked polymer of a partially neutralized α,β-ethylenically unsaturated monomer, the crosslinked polymer being crosslinked with a primary crosslinking agent selected from the groups consisting of, bis(acrylamido)acetic acid and its salts, allyl acrylate, allyl methacrylate and esters or amides having both a vinyl and an allyl functionality;

(b) contacting the crosslinked polymer with a surface crosslinking agent selected from the group consisting of polyhydroxy compounds, polyglycidyl ether compounds, polyfunctional aziridine compounds, polyfunctional amine compounds, and polyfunctional isocyanate compounds, under conditions such that the surface crosslinking agent coats the crosslinked polymer without substantial penetration into the interior of the crosslinked polymer to form a coated crosslinked polymer; and (c) heating the coated crosslinked polymer under conditions such that the surface crosslinking agent reacts with crosslinked polymer so as to crosslink the surface of the coated crosslinked polymer.

8. The process of claim 7, wherein the crosslinked polymer exists as a hydrogel comprising from about 20 to about 95 percent crosslinked polymer and from about 5 to about 80 percent water at the contacting of step (b).

9. The process of claim 7, wherein the crosslinked polymer exists as a powder having a moisture content less than about 5 weight percent at the contacting of step (b).

10. The process of claim 7, wherein the surface crosslinking agent is provided in a composition which comprises the surface crosslinking agent, and which optionally contains one or more constituents selected from the group consisting of water, an organic solvent, and a surfactant.

11. The process of claim 10, wherein the composition comprises from about 50 to about 100 percent polyhydroxy compound and from about 0 to about 50 percent water, the composition being free from organic solvent.

12. The process of claim 8, wherein the process further comprises:

(d) drying the coated crosslinked polymer, such that the water retained within the hydrogel is removed but such that the surface crosslinking agent does not react with the coated crosslinked polymer, the drying occurring after the contacting of step (b) but prior to the heating of step (c).

13. The process of claim 1, wherein the drying of step (b) occurs at a temperature from about 100° to about 175° C.

14. The process of claim 12, wherein the process further comprises:

(e) reducing the particle size of the coated crosslinked polymer by mechanical means after the drying of step (d) but before the heating of step (c).

15. The process of claim 14, wherein the reducing of the particle size results in average particle diameters less than about 0.8 mm.

16. The process of claim 8, wherein the process further comprises:

(d) drying the crosslinked polymer to a moisture content less than about 15 percent prior to the contacting of step (b).

17. The process of claim 16, wherein the drying of step (b) occurs at a temperature from about 100° to about 175° C.

18. The process of claim 16, wherein the process further comprises:

(e) reducing the particle size of the coated crosslinked polymer by mechanical means after the contacting of step (b) but before the heating of step (c).

19. The process of claim 18, wherein the reducing of the particle size results in average particle diameters less than about 0.8 mm.

20. The process of claim 7, wherein the heating occurs at a temperature from about 175° to about 210° C. for from about 5 to about 75 minutes.

21. The process of claim 7, wherein the surface crosslinking agent is provided at a level of at least about 200 ppm based on the weight of the water-absorbent resin.

22. The process of claim 7, wherein the surface crosslinking agent is provided at a level of at least about 500 ppm based on the weight of the water-absorbent resin.

23. The process of claim 7, wherein the surface crosslinking agent is provided at a level of at least about 1000 ppm based on the weight of the water-absorbent resin.

24. An aqueous fluid absorbent material produced in accordance with the process of claim 7.

25. A method for using the aqueous fluid absorbent material of claim 1 comprising incorporating the absorbent material into a personal care device.

* * * * *